United States Patent [19]
Bretton

[11] Patent Number: 5,620,013
[45] Date of Patent: Apr. 15, 1997

[54] METHOD FOR DESTROYING RESIDUAL LENS EPITHELIAL CELLS

[75] Inventor: Randolph H. Bretton, Maryland Heights, Mo.

[73] Assignee: American Cyanamid Company, Wayne, N.J.

[21] Appl. No.: 326,991

[22] Filed: Oct. 21, 1994

[51] Int. Cl.$^6$ .......................... A61B 19/00; A61K 38/00
[52] U.S. Cl. .................... 128/898; 514/2; 514/8; 514/12; 514/21; 514/23
[58] Field of Search ................. 514/2, 8, 12, 21, 514/23; 128/898

[56] References Cited

U.S. PATENT DOCUMENTS

| | | | |
|---|---|---|---|
| 4,432,751 | 2/1984 | Emery et al. | 604/49 |
| 4,515,794 | 5/1985 | Emery et al. | 514/249 |
| 4,657,930 | 4/1987 | Emery et al. | 514/557 |
| 4,847,240 | 7/1989 | Ryser et al. | 514/12 |
| 4,871,350 | 10/1989 | Lam et al. | 604/49 |
| 4,918,165 | 4/1990 | Soll et al. | 530/391 |
| 5,055,291 | 10/1991 | Lam et al. | 424/85.91 |
| 5,202,252 | 4/1993 | Emery et al. | 435/240.27 |
| 5,273,751 | 12/1993 | Dubroff | 424/427 |

OTHER PUBLICATIONS

"Biphasic Effect of the Mitotoxin bFGF–Saporin on Bovine Lens Epithelial Cell Growth: Effect of Cell Density and Extracellular Matrix", Thierry David, Jacqueline Tassin, Douglas A. Lappi, Andrew Baird, Yves Courtois, Journal of Cellular Physiology, 1992, pp. 483–490.

"Inhibition of Proliferating Lens Epithelium with Antitransferrin Receptor Immunotoxin", Kenneth M. Goins, MD; Julio R. Ortiz, MD; Sam F. A. Fulcher, MD; James T. Handa, MD; Glenn J. Jaffe, MD; Gary N. Foulks, MD; L. Michael Cobo, MD; J. Cararact Refract Surg, vol. 20, Sep. 1994, pp. 513–516.

Merck Manual, Fifteenth Ed., Merck & Co., Rahway, NJ, 1987. see pp. 1120–1121.

*Primary Examiner*—Christine M. Nucker
*Assistant Examiner*—Benet Prickril
*Attorney, Agent, or Firm*—Montgomery W. Smith; Rita D. Vacca

[57] ABSTRACT

A method for destroying residual lens epithelial cells in an eye in order to prevent the occurrence of posterior chamber opacification. A solution containing a basement membrane binding agent conjugated to a cytotoxic agent is introduced into the lens capsule. The solution is maintained in the lens capsule for a period of time sufficient to permit the basement membrane binding agent to bind to basement membranes within the lens capsule. The solution is then removed from the lens capsule, whereby a portion of the basement membrane binding agent remains bonded to basement membranes within the lens capsule, thereby exposing residual lens epithelial cells disposed on the basement membrane to the cytotoxic agent.

11 Claims, No Drawings

METHOD FOR DESTROYING RESIDUAL LENS EPITHELIAL CELLS

BACKGROUND OF THE INVENTION

The present invention relates to a method for destroying residual lens epithelial cells for the purpose of preventing the occurrence of posterior capsular opacification (PCO) or secondary cataract formation following the extracapsular extraction of a cataractous lens. More particularly, the present invention is directed to a method for destroying residual lens epithelial cells on the interior surface of the lens capsule of the eye through the application of membrane-binding agent having a toxin bonded thereto.

Cataract extraction is among the most commonly performed operations in the United States and the world. A cataractous lens is located within a capsular sac or lens capsule in the posterior chamber of the eye. In order to gain access to the cataractous lens, an incision typically is made at the limbus of the eye for the purpose of introducing a surgical instrument into the anterior chamber of the eye. In the case of extracapsular cataract extraction, a capsularhexis procedure is performed in which a portion of the anterior membrane of the lens capsule adjacent to the iris is removed using a surgical cutting instrument in order to provide direct access to the cataractous lens from the anterior chamber. The lens is then removed through various known methods, including phacoemulsification, a procedure which entails the application of ultrasonic energy to the lens in order to break the cataractous lens into small pieces which can be aspirated from the lens capsule. With the exception of the portion of the anterior membrane of the lens capsule removed during the capsularhexis procedure, the lens capsule remains substantially intact throughout an extracapsular cataract extraction. Following removal of the cataractous lens, an artificial intraocular lens typically is implanted within the lens capsule in order to mimic the refractive function of the original lens.

Although cataractous lens removal and intraocular lens implantation provide significant benefits to most cataract patients, it is estimated that up to fifty percent (50%) of all patients who have intraocular lenses implanted within the lens capsule will develop Posterior Capsular Opacification ("PCO") or secondary cataracts within five years after surgery. PCO is caused by the deposit of cells and fibers on the intraocular lens and on the posterior capsular membrane, thereby obstructing light passing through the intraocular lens and obscuring the patient's vision. These cell deposits originate from two sources: (1) the proliferation of residual lens epithelial cells on the interior surface of the lens capsule after surgery; and (2) the accumulation of inflammatory cells and protein deposits on the intraocular lens. Of these two sources, the major cause of PCO by far is the proliferation and migration of the residual lens epithelial cells on the capsular membrane.

Ophthalmic surgeons, aware of the problems associated with residual lens epithelial cells, typically take considerable care in trying to remove all residual lens epithelial cells prior to the implantation of an artificial intraocular lens. However, despite these efforts, a significant number of lens epithelial cells usually are left on the interior surface of the lens capsule due to the fact that these cells are difficult to identify and are often difficult to reach due to their position on the inside surface of the lens capsule.

The most common treatment for PCO entails the application of laser energy to the posterior membrane of the lens capsule for the purpose of destroying the lens epithelial cells propagating thereon. However, the laser energy applied to the posterior membrane of the lens capsule is ordinarily directed through the implanted intraocular lens, possibly resulting in damage to the optical and/or structural characteristics of the intraocular lens. The application of laser energy to the posterior membrane of the lens capsule also typically results in the destruction of a portion of the lens capsule as well as the residual lens epithelial cells propagating thereon. The destruction of a portion of the lens capsule creates a risk of exposure to the vitreous, possibly resulting in serious or irreparable damage to the eye. In addition, the destruction of a portion of the lens capsule creates a risk of shrinkage of the lens capsule, possibly resulting in a compromising of the optical characteristics of the intraocular lens. In certain cases, the destroyed posterior capsular tissue may regrow, e.g., as a result of a fibrin clot, thereby creating a renewed possibility of PCO. Accordingly, it is preferable to prevent the occurrence of PCO rather than attempting to treat it through the application of laser energy.

Various procedures for the prevention of PCO have been suggested in recent years. Many of these procedures have included the application of chemicals to the interior surface of the lens capsule in order to destroy residual lens epithelial cells. However, none of these procedures has proven to be particularly successful in the prevention of PCO due to the fact that it is extremely difficult to destroy residual lens epithelial cells without simultaneously destroying other cells within the eye, including the possible destruction of the corneal endothelium. Selective destruction of residual lens epithelial cells thus appears to be the key to the prevention of PCO.

Immunotoxins, hybrid molecules composed of a monoclonal antibody chemically linked to a toxic moiety, have been used in the selective destruction of residual lens epithelial cells. The monoclonal antibody directs the immunotoxin to the target cell. The cell then internalizes the immunotoxin, thereby causing the vital biological processes of the cell to be compromised by the toxic moiety. Other efforts have been made to destroy residual lens epithelial cells using a fibroblastic growth factor bonded to a toxic moiety. However, monoclonal antibodies and fibroblastic growth factors are relatively expensive and difficult to produce on a reliable and consistent basis. Therefore, it is desirable to employ a method that provides selective destruction of residual lens epithelial without the costs and problems associated with monoclonal antibodies.

SUMMARY OF THE INVENTION

The method of the present invention is used to destroy residual lens epithelial cells within the lens capsule following extracapsular cataract extraction through the use of a basement membrane binding agent. A cytotoxic agent capable of destroying residual lens epithelial cells preferably is conjugated to the basement membrane binding agent. Following extracapsular cataract extraction, the basement membrane binding agent conjugated to the cytotoxic agent is introduced into the lens capsule. The basement membrane binding agent conjugated to the cytotoxic agent is allowed to remain in the lens capsule for a predetermined period of time sufficient to permit the basement membrane binding agent to bind to the basement membranes within the lens capsule. Any excess material is then removed from the lens capsule. Residual lens epithelial cells disposed on the basement membranes are thus exposed to the cytotoxic agent conjugated to the basement membrane binding agent, resulting in the destruction of the residual lens epithelial cells.

In an alternative embodiment of the method of the present invention, a first basement membrane binding agent is introduced into the eye prior to performing a capsularhexis. The first basement membrane binding agent is allowed to remain in the eye for a predetermined period of time sufficient to permit the basement membrane binding agent to bind to the basement membranes within the eye. Excess of the first basement membrane binding agent is then removed from the eye. A capsularhexis and extracapsular cataract extraction is then performed, thus exposing additional basement membranes within the lens capsule. A second basement membrane binding agent having a cytotoxic agent conjugated thereto is then introduced into the eye and permitted to remain therein for a period of time sufficient to permit the basement membrane binding agent to bind to the basement membranes within the lens capsule. Any excess material is then removed from the eye. Residual lens epithelial cells disposed on the basement membranes within the lens capsule are thus exposed to the cytotoxic agent conjugated to the second basement membrane binding agent, resulting in the destruction of the residual lens epithelial cells.

DETAILED DESCRIPTION

The method of the present invention is intended to destroy residual lens epithelial cells disposed on the interior surfaces of the lens capsule, thereby preventing them from proliferating and/or migrating along the surface of the lens capsule and thereby preventing the occurrence of PCO. The method of the present invention can be employed in connection with any extracapsular cataract extraction procedure.

Extracapsular cataract extraction entails the formation of an incision through the eye in order to provide direct access to the anterior chamber of the eye. Although the necessary incision is usually formed at the limbus of the eye, it will be appreciated that alternative locations for this incision can be selected at the discretion of the surgeon. Following the formation of the incision, a cutting instrument is introduced through the incision into the anterior chamber of the eye. The cutting instrument is then advanced through the anterior chamber such that the cutting surface thereof is in the posterior chamber and in direct contact with the anterior surface of the lens capsule. A capsularhexis procedure is then performed, wherein a portion of the anterior membrane of the lens capsule is excised in order to provide direct access to the cataractous lens. The cataractous lens is then removed from the lens capsule. It will be appreciated that a variety of procedures can be used to remove the cataractous lens, including phacoemulsification and laser ablation. Upon removal of the cataractous lens from the lens capsule, an artificial intraocular lens is inserted into the eye for the purpose of mimicking the refractive characteristics of the natural lens. Intraocular lenses often are placed within the remaining portions of the lens capsule.

It has been discovered that certain agents will bind to the basement membranes, including basement membranes within the lens capsule of the eye. Because residual lens epithelial cells will be disposed on the basement membranes within the lens capsule, the basement binding agents, when bonded to the basement membrane, are in direct contact with the residual lens epithelial cells. The method of the present invention is based upon this discovery.

In a first embodiment of the method of the present invention, a solution containing a basement membrane binding agent is introduced into the lens capsule following extracapsular cataract extraction and prior to implantation of an artificial intraocular lens. In this first embodiment of the present invention, a cytotoxic agent is conjugated to the basement membrane binding agent. As above-discussed, the basement membrane binding agent will bind to the basement membranes that form the interior surface of the lens capsule, thereby providing direct contact between residual lens epithelial cells and the cytotoxic agent conjugated to the basement membrane binding agent. The solution containing basement membrane binding agent conjugated to the cytotoxic agent is retained within the lens capsule for a predetermined period of time sufficient to permit the basement membrane binding agent to bind to the basement membranes within the lens capsule. It will be appreciated that the length of time required for binding the basement membrane binding agent to the basement membranes within the lens capsule will be dependent upon a number of factors, including, but not limited to, the concentration of the basement membrane binding agent in the solution that is introduced into the lens capsule. Excess of the solution containing the basement membrane binding agent conjugated to the cytotoxic agent is then removed from the lens capsule. A variety of techniques can be used for the removal of this solution, including known aspiration and irrigation/aspiration techniques.

Following removal of the excess solution containing the basement membrane binding agent from the lens capsule, an intraocular lens can be implanted into the lens capsule using known implantation techniques. The incision in the eye is then closed and the procedure is complete.

It will be appreciated that the basement membrane binding agent will remain bonded to the basement membranes within the lens capsule. The cytotoxic agent conjugated to the basement membrane binding agent will thus have direct access to the residual lens epithelial cells on the interior surface of the lens capsule. In particular, it will be appreciated that the residual lens epithelial cells will come into contact with the basement membrane binding agent as the residual lens epithelial cells attempt to migrate across the interior surface of the lens capsule. The residual lens epithelial cells will internalize the cytotoxic agent, thereby resulting in the destruction of the residual lens epithelial cells on the interior surface of the lens capsule and thus preventing PCO.

It should be noted that the anterior chamber of the eye also includes basement membranes, e.g., the corneal endothelium. Due to the fact that corneal endothelium will not regenerate once it has been damaged, particular care should be exercised to ensure that the solution containing the basement membrane binding agent conjugated to a cytotoxic agent does not come into contact with the corneal endothelium. A second embodiment of the present invention is intended to protect the corneal endothelium from the effects of the cytotoxic agent.

In the second embodiment of the method of the present invention, a first solution containing a basement membrane binding agent without a cytotoxic agent conjugated thereto is introduced into the eye prior to performing a capsularhexis. The basement membrane binding agent in the first solution will bind to the exposed basement membranes within the eye, particularly the corneal endothelium. The first solution containing a basement membrane binding agent is allowed to remain in the eye for a predetermined period of time sufficient to ensure that adequate bonding has occurred between the first basement membrane binding agent and the basement membranes within the eye. It will be appreciated that the first solution will not come into contact with the interior of the lens capsule due to the fact that the lens capsule remains closed throughout this portion of the procedure. The first solution containing a basement membrane binding agent is then removed from the eye using known aspiration or irrigation/aspiration methods as above-discussed with respect to the first embodiment of the present invention. A capsularhexis procedure and an extracapsular cataract extraction procedure are then performed using known techniques.

A second solution containing a basement membrane binding agent conjugated to a cytotoxic agent is then introduced into the lens capsule. It is preferable that the second solution bind only to those basement membranes within the eye not previously bonded to the first basement membrane binding agent, thereby ensuring that the cytotoxic agent destroys residual lens epithelial cells within the lens capsule without damaging the corneal endothelium. For this reason, it is preferable that the first basement membrane binding agent be the same substance as the second basement membrane binding agent, thus ensuring that the first and second basement membrane binding agents bind to the same sites on the basement membranes.

Poly-lysine can be used as a basement membrane binding agent in connection with the method of the present invention. It will be appreciated that the molecular weight of poly-lysine or other polymeric basement membrane binding agents can be varied. This aspect of polymeric basement membrane binding agents makes them particularly beneficial when used in connection with the method of the present invention. In particular, it will be appreciated that the binding affinity of a polymeric basement membrane binding agent such as poly-lysine will increase as its molecular weight increases due to the increased number of binding sites available on the higher molecular weight molecule. Higher molecular weight poly-lysine molecules thus will tend to displace lower molecular weight poly-lysine molecules previously bonded to a basement membrane. For the above-discussed reasons, if a polymeric basement membrane binding agent such as poly-lysine is used in connection with the method of the present invention, it is preferable that the molecular weight of the first basement membrane binding agent be at least as great as the molecular weight of the second basement membrane binding agent in order to ensure that the second basement membrane binding agent does not displace the first basement membrane binding agent. In order to provide even greater assurances that the second basement membrane binding agent does not displace the first basement membrane binding agent, it is preferable that the molecular weight of the first basement membrane binding agent be greater than the molecular weight of the second basement membrane binding agent.

The second solution containing a basement membrane binding agent conjugated to a cytotoxic agent is retained within the lens capsule for a predetermined period of time sufficient to ensure that adequate bonding has occurred between the second basement membrane binding agent and the basement membranes not previously bonded to the first basement membrane binding agent. As above-discussed, the amount of time required is dependent upon a number of factors. Excess of the second solution is then removed from the eye using known techniques such as aspiration or irrigation/aspiration. An artificial intraocular lens can then be implanted in the eye. For the reasons discussed above with respect to the first embodiment of the present invention, the cytotoxic agent will tend to destroy residual lens epithelial cells within the lens capsule, thereby preventing PCO.

In a third embodiment of the present invention, the above-described steps of the first embodiment of the invention are performed. Next, a second solution containing a second basement membrane binding agent is provided and is introduced into the eye for the purpose of displacing any of the first basement membrane binding agent that may have come into contact with the corneal endothelium. For the above-discussed reasons, it is preferable that the second basement membrane binding agent be the same substance as the first basement membrane binding agent. In addition, it is preferable that the molecular weight of the second basement membrane binding agent be greater than the molecular weight of the first basement membrane binding agent, thereby ensuring that the second basement membrane binding agent will displace the first basement membrane binding agent on the corneal endothelium.

A variety of basement membrane binding agents can be used in connection with the method of the present invention. In a preferred embodiment of the present invention poly-lysine is employed as a basement membrane binding agent. Poly-L-lysine has been shown to be effective when used in connection with the method of the present invention. It is possible that poly-D-lysine also can be effective. Poly-lysine is advantageously used in connection with the present invention due to its availability, relatively low cost, and its ability to be formulated in a variety of molecular weights. Other basement membrane binding agents believed to be useful in connection with the present invention include, but are not limited to, fibronectin, laminin, type IV collagen, perlecan, decorin, thrombospondin, tenascin, vitronectin, heparin, heparan sulfate, poly-arginine, dextran, dextran sulfate, chondroitan sulfate, hyaluronic acid, platelet factor IV, fibrin, and fibrinogen.

A variety of known cytotoxic agents can be used in conjunction with the method of the present invention. In a preferred embodiment of the present invention, a ribosomal inhibitory protein such as saporin or ricin is used as the cytotoxic agent. Ribosomal inhibitory proteins are preferable due to the fact that they contain more inhibitory activity per microgram than other cytotoxic agents that can be used in connection with the method of the present invention. Other cytotoxic agents believed to be efficacious when used in connection with the method of the present invention include, but are not limited to, antimitotic drugs such as methotrexate, 5-fluorouracil, daunomycin, doxorubicin, mitoxanthrone, vinca alkaloids, vinblastine, colchicine, or cytochasins, are used as the cytotoxic agent. In addition, ionophores such as monensin and ouabain can be used as the cytotoxic agent in connection with the method of the present invention. It will be appreciated that antimitotic conjugates will destroy proliferating lens epithelial cells while exhibiting less toxicity to the iris and corneal endothelium compared to the ribosomal inhibitory proteins.

A variety of known methods can be employed for conjugating the cytotoxin to the basement membrane binding agent. For example, the carboxyl groups of the cytotoxic agent can be bonded to the amines of the basement membrane binding agent using a water-soluble carbodiimide technique. When this technique for conjugation is used, the entire conjugate will be internalized by the residual lens epithelial cells and the basement membrane binding agent will then be degraded by the cell to release the cytotoxic agent.

Hetero-bi-functional cross-linkers such as SPDP also can be used to conjugate the cytotoxic agent to the basement membrane binding agent, thereby creating a disulfide bond between the cytotoxic agent and the basement membrane binding agent. Once the resulting hybrid molecule is internalized by the residual lens epithelial cell, the disulfide bond is hydrolyzed to release the cytotoxic agent, thereby resulting in the destruction of the cell.

It is believed that recombinant DNA technology also can be used to construct the gene for a toxin with a basement membrane binding protein sequence incorporated therein. This gene may be expressed in a host cell and the product purified from the growth medium.

By way of example and not by way of limitation, a conjugate of poly-lysine and saporin was prepared by coupling poly-lysine to SPDP in accordance with the instructions stated by the manufacturer of the SPDP. The free SPDP was then removed using a filtration technique or, in the alternative, through the use of a sepharose heparin column. The resulting poly-lysine-SPDP was then reduced with dithiothreatol. Saporin was then coupled with SPDP in the same manner and added to the solution of poly-lysine-SPDP. The resulting solution filtered to remove uncoupled agents, thereby producing a conjugated poly-lysine-saporin solution.

The solution containing the basement membrane binding agent can comprise a variety of known biocompatible agents. In one embodiment of the present invention, the basement membrane binding agent is contained in a balanced salt solution. Solutions containing viscoelastics such as methylcellulose also can be used in connection with the present invention. It will be appreciated that other known biocompatible solutions can be used in connection with the method of the present invention.

Although the present invention has been described herein with respect to certain preferred embodiments, it will be appreciated by one of ordinary skill in the pertinent art that various modifications can be made without departing from the intended spirit and scope of the invention.

What is claimed is:

1. A method for destroying residual lens epithelial cells in a lens capsule of an eye following extracapsular cataract extraction, said method comprising:

providing a first solution containing a first basement membrane binding agent, polylysine, conjugated to a cytotoxic agent, saporin;

introducing said first solution into said lens capsule;

maintaining said first solution in said lens capsule for a predetermined period of time sufficient for said first basement membrane binding agent to bind to a basement membrane within said lens capsule; and removing said first solution from said lens capsule, whereby residual lens epithelial cells on said basement membrane within said lens capsule are exposed to said first basement membrane binding agent conjugated to a cytotoxic agent such that said residual lens epithelial cells internalize said first basement membrane binding agent conjugated to a cytotoxic agent, and whereby said residual lens epithelial cells are destroyed by said cytotoxic agent.

2. A method for destroying residual lens epithelial cells in a lens capsule following extracapsular cataract extraction in accordance with claim 1, wherein said first solution comprises a balanced salt solution.

3. A method for destroying residual lens epithelial cells in a lens capsule following extracapsular cataract extraction in accordance with claim 1, wherein said first solution comprises a viscoelastic material.

4. A method for destroying residual lens epithelial cells in a lens capsule following extracapsular cataract extraction in accordance with claim 1, wherein said cytotoxic agent is conjugated to said first basement membrane binding agent using a water soluble carbodiimide technique.

5. A method for destroying residual lens epithelial cells in a lens capsule following extracapsular cataract extraction in accordance with claim 1, wherein said cytotoxic agent is conjugated to said first basement membrane binding agent using a hetero-bi-functional cross-linker.

6. A method for destroying residual lens epithelial cells in a lens capsule following extracapsular cataract extraction in accordance with claim 1, wherein said method further comprises:

providing a second solution containing a second basement membrane binding agent polylysine, said second basement membrane binding agent having a molecular weight greater than a molecular weight of said first basement membrane binding agent;

introducing said second solution onto corneal endothelial basement membranes within an anterior chamber of said eye following removal of said first solution from said eye, whereby said second basement membrane binding agent displaces said first basement membrane binding agent to the extent that any of said first basement membrane binding agent has bonded to said corneal endothelial basement membranes, thereby preventing damage to said corneal endothelial basement membranes; and removing said second solution from said eye.

7. A method for destroying residual lens epithelial cells in a lens capsule of an eye, said method comprising:

providing a first solution containing a first basement membrane binding agent, said first basement membrane binding agent being polylysine;

introducing said first solution into said eye prior to performing a capsularhexis and prior to removing a cateractous lens from said eye;

maintaining said first solution in said eye for a predetermined period of time sufficient for said first basement membrane binding agent to bind to a basement membrane within an anterior chamber of said eye;

removing said first solution from said eye;

performing a capsularhexis;

removing said cataractous lens from said eye;

providing a second solution containing a second basement membrane binding agent, polylysine conjugated to a cytotoxic agent, saporin;

introducing said second solution into said lens capsule;

maintaining said second solution in said lens capsule for a predetermined period of time sufficient for said second basement membrane binding agent to bind to a basement membrane within said lens capsule; and removing said second solution from said lens capsule, whereby residual lens epithelial cells on said basement membrane within said lens capsule are exposed to said second basement membrane binding agent conjugated to a cytotoxic agent such that said residual lens epithelial cells internalize said second basement membrane binding agent conjugated to a cytotoxic agent, and whereby said residual lens epithelial cells are destroyed by said cytotoxic agent.

8. A method for destroying residual lens epithelial cells in a lens capsule in accordance with claim 7 wherein said first solution and said second solution comprise a balanced salt solution.

9. A method for destroying residual lens epithelial cells in a lens capsule in accordance with claim 7, wherein said first solution comprises a viscoelastic material.

10. A method for destroying residual lens epithelial cells in a lens capsule in accordance with claim 7, wherein said cytotoxic agent is conjugated to said second basement membrane binding agent using a water soluble carbodiimide technique.

11. A method for destroying residual lens epithelial cells in a lens capsule in accordance with claim 7, wherein said cytotoxic agent is conjugated to said second basement membrane binding agent using a hetero-bi-functional cross-linker.

* * * * *